United States Patent
Ren

(10) Patent No.: US 7,982,110 B2
(45) Date of Patent: Jul. 19, 2011

(54) ECHINACEA PURPUREA G0052Y

(75) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 242 days.

(21) Appl. No.: 12/258,179

(22) Filed: Oct. 24, 2008

(65) Prior Publication Data

US 2010/0107266 A1    Apr. 29, 2010

(51) Int. Cl.
*A01H 1/00* (2006.01)
*A01H 5/00* (2006.01)
*A01H 5/10* (2006.01)
*C12N 15/82* (2006.01)

(52) U.S. Cl. ........ 800/323; 435/410; 800/260; 800/298; 800/300

(58) Field of Classification Search ............... Plt./428
See application file for complete search history.

(56) References Cited

U.S. PATENT DOCUMENTS

PP12,242 P2 * 12/2001 Hawks .................... Plt./428

OTHER PUBLICATIONS

John M. Poehlman et al., 1995. Breeding Field Crops, Fourth Edition. Iowa State University Press / Ames. pp. 172-175.

Neil O. Anderson, 2006. Flower Breeding and Genetics. Chapter 30, Springer, The Netherlands. pp. 799-822.
CPVO Database, CPVR Application 20100957 of Ball Horticultural Company, filed May 5, 2010.

* cited by examiner

*Primary Examiner* — David H Kruse
(74) *Attorney, Agent, or Firm* — Jondle & Associates, P.C.

(57) ABSTRACT

The present invention relates to an *Echinacea* plant, seed, variety and hybrid. More specifically, the invention relates to an *Echinacea* plant having a compact, well-branched plant, having bright, deep rose-colored flowers. The invention relates to the seeds of *Echinacea purpurea* G0052Y, to the plants of *Echinacea purpurea* G0052Y, to plant parts of *Echinacea purpurea* G0052Y and to methods for producing an *Echinacea* plant produced by crossing *Echinacea purpurea* G0052Y with itself or with another *Echinacea* variety or hybrid. The invention also relates to methods for producing an *Echinacea* plant containing in its genetic material one or more transgenes and to the transgenic *Echinacea* plants and plant parts produced by those methods. This invention also relates to *Echinacea* cultivars or hybrids and plant parts derived from *Echinacea purpurea* G0052Y, to methods for producing other *Echinacea* cultivars, lines, hybrids or plant parts derived from *Echinacea purpurea* G0052Y and to the *Echinacea* plants, varieties, hybrids and their parts derived from use of those methods. The invention further relates to hybrid *Echinacea* seeds, plants and plant parts produced by crossing plants of *Echinacea purpurea* G0052Y with another *Echinacea* plant.

17 Claims, No Drawings

ECHINACEA PURPUREA G0052Y

TECHNICAL FIELD

This invention is in the field of *Echinacea* breeding, specifically relating to a novel *Echinacea purpurea* line designated G0052Y and progeny therefrom.

BACKGROUND OF THE INVENTION

*Echinacea*, commonly known as coneflower, is a member of the Asteraceae family. According to the most widely accepted taxonomic treatment, the genus *Echinacea* is composed of eleven taxa, nine North American indigenous species and two varieties [See McGregor, R. L., *Univ. Of Kansas Science Bulletin* 48(4):113-142 (1968).] This article and all publications cited in this application are herein incorporated by reference.

*Echinacea* has a rich tradition of medicinal use by North American Plains Indians. Currently, three of the species, *E. angustifolia, E. pallida*, and *E. purpurea*, have commercial value as herbal remedies for general immune-boosting effects. These species along with *E. paradoxa* and *E. tennesseensis* are also of ornamental value and grown as popular landscape plants and cut flowers.

*Echinacea* are herbaceous perennial plants having basal rosette of leaves and erect flowering stems. The flower heads have many fertile disc florets borne on a flattened to raised receptacle, and typically have a single outer whorl of sterile ray florets. The flower heads have a bristly appearance due to the stiff, sharp palea subtending the disc florets. As a garden perennial, *E. purpurea* is most common, and has flower colors restricted to purple through pink shades to white. Hybridization with yellow flowered *E. paradoxa* has broadened the color range [See Rice, G., *Plantsman* 212-219 (2007).]

*Echinacea* can be propagated from seed, cuttings, divisions, and through tissue culture. Seed germination protocols for several of the species are now well known in the art [See Ault, J. R., Coneflower, *Echinacea* species, p. 799-822. In: Flower Breeding and Genetics: Issues, Challenges, and Opportunities for the 21st Century, Anderson, N. O., ed., The Netherlands, Springer, (2006).]

Hybridization studies revealed that *Echinacea* species hybridize easily and many fertile $F_1$ hybrids can be produced. *Echinacea* breeding has barriers. Historically, the genus was described as being completely self-incompatible. A later study of *E. angustifolia* reported up to 9% self-pollinations. While the degree and type of self-incompatibility remains unknown, breeding strategies employing mass selection or phenotypic recurrent selection offer models for the development and maintenance of *Echinacea* seed lines [See Ault, J. R., Coneflower, *Echinacea* species, p. 799-822. In: Flower Breeding and Genetics: Issues, Challenges, and Opportunities for the 21st Century, Anderson, N. O., ed., The Netherlands, Springer, (2006).]

With any successful breeding program, there are numerous steps in the development of novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. For the horticultural industry, these important traits can include novel colors, resistance to diseases and insects, tolerance to drought and heat, or superior garden performance.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits can be used as parents to produce new populations for further selection.

These processes, which lead to the final step of marketing and distribution, require several from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above-described problems have been reduced or eliminated, while other embodiments are directed to other improvements. Other limitations of the related art will become apparent to those of skill in the art upon a reading of the specification. The use of the article "a" or "an" is intended to include one or more.

The present invention relates to *Echinacea purpurea* plants designated G0052Y. Plants of *Echinacea purpurea* G0052Y are further valued as breeding lines enabling the development of superior ornamental *Echinacea* hybrid plants having a range of desirable, brightly colored flowers, and superior garden performance.

The present invention further provides plants, seeds, and other plant parts such as pollen and ovules of *Echinacea purpurea* G0052Y. This invention thus relates to the seeds of *Echinacea purpurea* G0052Y, to the plants of *Echinacea purpurea* G0052Y and to methods for producing an *Echinacea purpurea* plant produced by crossing *Echinacea purpurea* G0052Y with itself or another *Echinacea* species, and the creation of variants by mutagenesis or transformation of *Echinacea purpurea* G0052Y.

Thus, any such methods using *Echinacea purpurea* G0052Y are part of this invention: selfing, backcrosses, hybrid production, crosses to populations, and the like. All plants produced using *Echinacea purpurea* G0052Y as at least one parent are within the scope of this invention. Advantageously, *Echinacea purpurea* G0052Y could be used in crosses with other, different, *Echinacea* plants to produce first generation ($F_1$) *Echinacea* hybrid seeds and plants with superior characteristics.

In another aspect, the present invention provides for single or multiple gene converted plants of *Echinacea purpurea* G0052Y. The transferred gene(s) may preferably be a dominant or recessive allele. Preferably, the transferred gene(s) will confer such traits as herbicide tolerance; insect resistance; resistance to bacterial, fungal, nematode or viral disease; male sterility and restoration of male fertility. The gene may be a naturally occurring *Echinacea* gene or a transgene introduced through genetic engineering techniques.

In another aspect, the present invention provides regenerable cells for use in tissue culture of *Echinacea purpurea* G0052Y. The tissue culture will preferably be capable of regenerating plants having all the physiological and morphological characteristics of the foregoing *Echinacea* plant, and of regenerating plants having substantially the same genotype as the foregoing *Echinacea* plant. Preferably, the regenerable cells in such tissue cultures will be embryos, protoplasts, meristematic cells, callus, pollen, leaves, anthers, pistils, stems, petioles, roots, root tips, seeds, flowers, cotyledons, hypocotyls or the like. Still further, the present invention provides *Echinacea* plants regenerated from the tissue cultures of the invention.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Allele. "Allele" is any of one or more alternative forms of a gene, all of which alleles relate to one trait or characteristic. In a diploid cell or organism, the two alleles of a given gene occupy corresponding loci on a pair of homologous chromosomes.

Diploid. A diploid is a cell or organism having a pair of each type of chromosome (homologous pair), so that the basic chromosome number is doubled.

Essentially all the physiological and morphological characteristics. A plant having "essentially all the physiological and morphological characteristics" means a plant having the physiological and morphological characteristics, except for the characteristics derived from the converted gene.

Plant. "Plant" includes plant cells, plant protoplasts, plant cells of tissue culture from which petunia plants can be regenerated, plant calli, plant clumps and plant cells that are intact in plants or parts of plants such as pollen, flowers, pistils, anthers, seeds, leaves, stems, and the like.

Quantitative Trait Loci (QTL). "Quantitative trait loci (QTL)" refer to genetic loci that control to some degree numerically representable traits that are usually continuously distributed.

Regeneration. "Regeneration" refers to the development of a plant from tissue culture.

Single gene converted (conversion). "Single gene converted" (or conversion) plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Transgenic. "Transgenic" refers to a line has been converted to contain one or more transgenes by single gene conversion or by direct transformation.

DETAILED DESCRIPTION OF THE INVENTION

The following examples are set forth as representations of specific and preferred embodiments of the present invention. These examples are not to be construed as limiting the scope of the invention in any manner. It should be understood that many variations and modifications can be made while remaining within the spirit and scope of the invention.

The present invention relates to *Echinacea purpurea* plants designated G0052Y, having a compact, well-branched plant habit and having bright deep rose-colored flowers valued as an ornamental plant in the landscape. The present invention also relates to an *Echinacea* seed, an *Echinacea* plant and plant parts derived from G0052Y. The present invention also relates to an *Echinacea* hybrid and plant parts derived from G0052Y. The present invention also relates to a method of producing the disclosed *Echinacea* and *Echinacea* hybrid plants and seeds.

The present invention also relates to methods for producing an *Echinacea* plant or hybrid plant derived from G0052Y and containing in its genetic material one or more transgenes and to the transgenic *Echinacea* plant or hybrid plant produced by that method.

The invention further provides methods for developing *Echinacea* plants and *Echinacea* hybrid plants in a plant breeding program using plant breeding techniques including parental selection and hybrid development, recurrent selection, backcrossing, pedigree breeding, restriction fragment length polymorphism enhanced selection, genetic marker enhanced selection and transformation. Seeds, *Echinacea* plants, and parts thereof produced by such breeding methods are also part of the invention.

EXAMPLES

Example 1

Development of G0052Y

The present invention arose from a cross in 2001 between a plant of *Echinacea purpurea* 'Magnus', not patented, and a plant of *Echinacea purpurea* 'Kim's Knee High', U.S. Plant Pat. No. 12,242. Hybrid seed collected from this cross were planted in the spring of 2002, and grown in both greenhouse and field locations. The progeny plants were tall and vigorous with a purple ray floret color that was characteristic of the parent *Echinacea purpurea* plants. In July 2002, eleven progeny plants in the greenhouse location were selected, and individual plants were designated E05-1 through E05-11. Pollen was collected from all eleven plants and mixed. The mixed pollen was used to pollinate all eleven plants that were functioning as female plants. Seeds were harvested and maintained separately from each female.

In 2003, seeds from plants E05-1 through E05-11 were grown into eleven populations and evaluated in the field. The progeny populations segregated for height, branching and color. For ray floret color, three types were observed: the purple characteristic of the parent *Echinacea purpurea* plants, white, and a deep rose. It is currently believed by those skilled in the art that for *Echinacea purpurea*, tall is dominant to short, fewer branches are dominant to more branches, and the purple ray floret color is dominant to both deep rose and white flowers, with deep rose being dominant to white. In six out of the eleven families, plants segregated for the purple ray floret color characteristic of the parent *Echinacea purpurea* plants and deep rose. In the other five out of the eleven families plants segregated for the purple ray floret color characteristic of the parent *Echinacea purpurea* plants, deep rose, and white. In all eleven families, individual plants were observed having horticulturally desirable traits of a very bright, deep rose ray floret color, wide ray florets, less gapping between the florets, short and compact habit, increased branching, early flowering, and floriferousness. It was unexpected that the ray color appeared bright, unlike the parental material. Twenty-two plants, designated E05-1-1 through E05-1-6, E05-2-3, E05-2-4, E05-3-3, E05-4-1, E05-4-2, E05-4-3, E05-6-1, E05-8-1, E05-10-1, E05-10-2, and E05-11-1 through E05L-11-6 having the very bright, deep rose ray floret color and horticulturally desirable traits were selected. Pollen was collected from all twenty plants and mixed. The mixed pollen was used to pollinate all twenty plants that were functioning as female plants. Seeds were harvested and maintained separately from each female.

The families of progeny seeds were sown in 2004 and evaluated in field conditions. Thirteen of the twenty-one families segregated for very bright, deep rose and white ray floret color, with a ratio of approximately 5:1 for deep rose: white. Thirty-one of the plants having the very bright, deep rose ray floret color and horticulturally desirable traits were selected and designated as E05-1-5-1, E05-1-6-1, E05-1-6-2, E05-2-3-1 through E05-2-3-6, E05-2-4-1, E05-4-1-1, E05-4-1-2, E05-4-1-3, E05-4-2-1, E05-8-1-1, E05-10-1-1, E05-10-2-1, E05-10-2-2, E05-10-2-3, E05-11-1-1, E05-11-1-2, E05-11-2-1, E05-11-3-1, E05-11-4-1, E05-11-4-2, E05-11-4-3, E05-11-5-1, E05-11-5-2, E05-11-5-3, E05-11-7-1, and E05-11-7-2. Progeny test crosses and recessive color test crosses identified four sib plants E05-2-3-2, E05-4-1-3, E0511-4-2, and E05-11-4-3 as being homozygous for very bright, deep rose ray floret color. These sib plants were phenotypically identical. In 2005, the four sib plants were combined through mass crossing to create a uniform line which was designated G0052Y.

Example 2

The Characteristics of *Echinacea purpurea* G0052Y

During the 2006, 2007, and 2008 summers, G0052Y was trialed under field conditions to the closest known commercial comparison *Echinacea purpurea* 'Magnus'. Plants were grown at a research facility located at Elbum, Ill. For the 2007 trial, plants were transplanted to the field on May 18, 2007 and the data was collected from fully mature plants on Sep. 5, 2007. Data is shown in Table 1 below. The chart used in the identification of colors described herein is The R.H.S. Colour Chart of The Royal Horticultural Society, London, England, 2001 edition, except where general color terms of ordinary significance are used. The color values were determined under natural light conditions. Measurements and numerical values represent averages of typical plants.

Also during the summer of 2007, field comparisons between other commercially available varieties including 'Bravado', 'Bright Star', 'Deep Rose', and 'Primadonna Deep Rose' were made. In these, G0052Y was shown to have a deeper rose ray floret color, significantly increased branching, shorter plant height, more compact habit, and to be earlier to flower by approximately 20 days in comparison to these varieties.

TABLE 1

Detailed description of *Echinacea purpurea* G0052Y compared with *Echinacea purpurea* 'Magnus'.

| *Echinacea purpurea* G0052Y | *Echinacea purpurea* 'Magnus' |
|---|---|
| A. GENERAL INFORMATION | A. GENERAL INFORMATION |
| Life Cycle: Perennial | Life Cycle: Perennial |
| Use: Outdoor (bedding) | Use: Outdoor (bedding) |

TABLE 1-continued

Detailed description of *Echinacea purpurea* G0052Y compared with *Echinacea purpurea* 'Magnus'.

| *Echinacea purpurea* G0052Y | *Echinacea purpurea* 'Magnus' |
|---|---|
| Ploidy: Diploid<br>Type of Variety: Open-pollinated | Ploidy: Diploid<br>Type of Variety: Open-pollinated |
| B. PLANT | B. PLANT |
| Form: Upright Branching<br>Branching: Basally Branching<br>Growth Form: Upright<br>Plant Width (at widest point): 54.3 cm<br>Plant Height (from soil level to top of inflorescence): 52.4 cm<br>Plant Height Class: Semi-Dwarf<br>Stem Thickness: 4.0 mm, Ribbed<br>Main Stem Color: Medium Green, RHS 144B<br>Stem Anthocyanin: Weak<br>Stem Strength: Not Brittle<br>Stem Flexibility: Rigid<br>Stem Vesture: Pubescent | Form: Upright Branching<br>Branching: Basally Branching<br>Growth Form: Upright<br>Plant Width (at widest point): 70.0 cm<br>Plant Height (from soil level to top of inflorescence): 74.6 cm<br>Plant Height Class: Tall<br>Stem Thickness: 6.0 mm, Ribbed<br>Main Stem Color: Medium Green, RHS 144B<br>Stem Anthocyanin: Weak<br>Stem Strength: Not Brittle<br>Stem Flexibility: Rigid<br>Stem Vesture: Pubescent |
| C. FOLIAGE | C. FOLIAGE |
| Width (at midpoint of plant): 4.4 cm<br>Length (at midpoint of plant, including petiole): 17.9 cm<br>Petiole Length: 4.1 cm.<br>Leaf Attachment: Both Sessile and Petiolate<br>Leaf Attitude: Reflexed<br>Leaf Shape: Lanceolate<br>Leaf Margin: Serrate<br>Margins: Undulated<br>Leaf Surface: Weakly Bubbled<br>Leaf Apex: Pointed<br>Leaf Anthocyanin: Weak<br>Upper Foliage Surface<br>Color: Dark Green, RHS 137A<br>Surface Luster: Dull<br>Surface Pubescence: Medium<br>Lower Foliage Surface<br>Color: Medium Green, Closest to RHS 138B<br>Surface Luster: Dull<br>Surface Pubescence: Medium | Width (at midpoint of plant): 6.3 cm<br>Length (at midpoint of plant, including petiole): 15.0 cm<br>Petiole Length: 2.0 cm.<br>Leaf Attachment: Both Sessile and Petiolate<br>Leaf Attitude: Reflexed<br>Leaf Shape: Lanceolate<br>Leaf Margin: Serrate<br>Margins: Undulated<br>Leaf Surface: Weakly Bubbled<br>Leaf Apex: Pointed<br>Leaf Anthocyanin: Weak<br>Upper Foliage Surface<br>Color: Dark Green, RHS 137A<br>Surface Luster: Dull<br>Surface Pubescence: Medium<br>Lower Foliage Surface<br>Color: Medium Green, Closest to RHS 138B<br>Surface Luster: Dull<br>Surface Pubescence: Medium |
| D. MATURITY | D. MATURITY |
| Days from Sowing to First Flowering: Approximately 150 | Days from Sowing to First Flowering: Approximately 170 |
| E. INFLORESCENCE | E. INFLORESCENCE |
| Inflorescence Type: Solitary Flowers<br>Flower Head Shape: Convex<br>Flower Head Symmetry: Symmetrical<br>Flower Fullness: Single<br>Width: 7.4 cm<br>Depth: 6.1 cm<br>Number of Fully-Open Inflorescences per Plant: 21<br>Fragrance: Mild<br>Peduncle Color: Green, RHS 144B<br>Peduncle Length: 12.0 cm<br>Ray Floret<br>Dorsal Side Pubescence: Glabrous<br>Ventral Side Pubescence: Glabrous<br>Dorsal Side Luster: Dull<br>Ventral Side Luster: Dull<br>Petal Twisted: Absent (Flat)<br>Parallel Furrows: Deep<br>Petal Shape: Broad strap<br>Petal Type: Straight, Recurved with age<br>Petal Apex: Acute<br>Petal Apex Margin: Retuse | Inflorescence Type: Solitary Flowers<br>Flower Head Shape: Convex<br>Flower Head Symmetry: Symmetrical<br>Flower Fullness: Single<br>Width: 10.2 cm<br>Depth: 7.0 cm<br>Number of Fully-Open Inflorescences per Plant: 13<br>Fragrance: Mild<br>Peduncle Color: Green, RHS 144B<br>Peduncle Length: 13.8 cm<br>Ray Floret<br>Dorsal Side Pubescence: Glabrous Ventral Side Pubescence: Glabrous Dorsal Side Luster: Dull<br>Ventral Side Luster: Dull<br>Petal Twisted: Absent (Flat)<br>Parallel Furrows: Deep<br>Petal Shape: Strap<br>Petal Type: Straight, Recurved with age<br>Petal Apex: Acute<br>Petal Apex Margin: Retuse<br>Petal Color: Purple, RHS 70B, Fades with |

TABLE 1-continued

Detailed description of *Echinacea purpurea* G0052Y compared with *Echinacea purpurea* 'Magnus'.

| *Echinacea purpurea* G0052Y | *Echinacea purpurea* 'Magnus' |
|---|---|
| Petal Color: Deep Rose, RHS 64A, Fades with age to RHS 64B | age to slightly lighter than RHS 70B |
| Ray Floret Length: 3.5 cm | Ray Floret Length: 5.0 cm |
| Ray Floret Width: 1.2 cm | Ray Floret Width: 1.2 cm |
| Disk Floret | Disk Floret |
| Form: Present, Uncovered | Form: Present, Uncovered |
| Disk Floret Color: Base of RHS 155D, transitions to a mid-section of RHS 144A with a scarlet-red apex of RHS 46A | Disk Floret Color: Base of RHS 155D, transitions to a mid-section of RHS 144A with a scarlet-red apex of RHS 46A |
| Disk Floret Length (longest Disk Floret): 8.0 mm | Disk Floret Length (longest Disk Floret): 9.0 mm |
| Bract Length: 1.3 cm | Bract Length: 1.4 cm |
| Bract Color: Scarlet-red RHS 44B, Darkens with age to RHS 46A | Bract Color: Scarlet-red RHS 44B, Darkens with age to RHS 46A |

| F. SEEDS | F. SEEDS |
|---|---|
| Seed Length: 4.0 mm | Seed Length: 5.0 mm |
| Seed Width: 2.0 mm | Seed Width: 2.0 mm |
| Seed Thickness: 2.0 mm | Seed Thickness: 2.0 mm |
| Weight per 100 Seeds: 0.372 grams | Weight per 100 Seeds: 0.414 grams |
| Seed Coat Color: Brown, 199C | Seed Coat Color: Brown, Lighter than 199D |

Example 3

Interspecific Hybridization of G0052Y Parental Line and *Echinacea tennesseensis*

In 2003, the plant designated E05-1 was crossed with an *Echinacea tennesseensis* plant designated as Ball Accession No. 4723. E05-1 was in the pedigree of G0052Y as noted in Example 1. The species *Echinacea tennesseensis* is characterized by dark purple-colored, slightly curved ray florets having a very narrow and gapping appearance. The plants are typically tall and flower relatively early when compared to other *Echinacea* species. The seeds from the cross were collected and sown and the resulting $F_1$ plants were grown in field in 2004. Unexpectedly, the progeny exhibited dark purple-colored ray florets that were more perpendicular to the inflorescence axis than is typical of the species *Echinacea tennesseensis*. In addition the plants were unexpectedly, very floriferous with multiple flower heads, fairly good branching, and early to flower. The height of the plants was intermediate between the two parent plants.

Example 4

Interspecific Hybridization of G0052Y Parental Lines and *Echinacea paradox*

In 2003, plants designated E05-3, E05-4, and E05-10 were crossed to an *Echinacea paradoxa* plant designated Ball Accession No. 4353. Plants designated E05-3, E05-4, and E05-10 were in the pedigree of G0052Y. The species *Echinacea paradoxa* is characterized by dark yellow-colored, drooping ray florets having a narrow and gapping appearance. Typically *Echinacea paradoxa* plants are very tall with an open and poorly branched growth habit, and cannot flower in the first year after sowing. Seeds from the cross were collected and sown and the resulting $F_1$ plants were grown in the field in 2004. Unexpectedly, the progeny exhibited large, narrow, purple-pink colored ray florets. Unexpectedly, the plants were tall with an open and poorly branched growth habit. Many of the $F_1$ plants did not flower in the first year after planting.

Five $F_1$ plants were selected with relatively better horticulturally desired traits than the *Echinacea paradoxa* parent and designated E10-1 through E10-5. These plants were massed as previously described. In addition, plants designated E10-1 through E10-5 were crossed with the commercial varieties *Echinacea hybrida* 'Art's Pride', U.S. Plant Pat. No. 15,090, *Echinacea hybrida* 'Sunset', U.S. Plant Pat. No. 16,424, and *Echinacea hybrida* 'Sunrise', U.S. Plant Pat. No. 16,235. Seeds were harvested from the mass and hybrid crosses, sowed and grown in field conditions in 2005. The progeny plants segregated for orange, creamy-yellow, and purple ray floret color.

Of the progeny, twenty-four $F_2$ plants were selected having shades of orange and shades of yellow ray floret colors and were designated E18-1 through E18-24. Unexpectedly, these plants exhibited a growth habit more like that of the species *Echinacea paradoxa* than of *Echinacea purpurea*. In addition, they unexpectedly had relatively narrow foliage and were later to flower. Also observed were unexpected orange shades of ray floret color having horticultural interest. These twenty-four $F_2$ plants were massed, seeds were harvested, sown, and progeny were grown in field conditions in 2006. The progeny $F_3$ plants continued to segregate for shades of orange and shades of yellow ray floret colors. Unexpectedly, these plants continuously exhibited the narrow foliage and tall, open habit.

Also in 2005, eighteen $F_2$ plants were selected out of the twenty-four plants designated E18-1 through E18-24 and were individually backcrossed with pollen from G0052Y. Seeds were harvested, sown, and the $F_2BC_1$ progeny were grown in field conditions in 2006. Most of the plants were very well branched, early to flower and had a compact growth habit. The $F_2BC_1$ plants had a dark purple ray floret color.

Twenty-five $F_2BC_1$ plants designated E23-1 through E23-8, E24-1 through E24-4, E25-1, E25-2, E26-1 through E26-8, E27-1, E27-2, and E27-3 were selected and massed, seeds were harvested, sown, and the progeny were grown in field conditions in 2007. The progeny plants of $F_2BC_1$ segregated for deep purple, deep rose, deep red purple, deep orange, bright orange, red orange, red, coral, coral purple, dark yellow, and creamy yellow ray floret color. It was unexpected that the observed ray floret colors were much deeper and brighter than the parent plants. In addition, the plants were unexpectedly early to flower, with ray florets that were wider and flatter, without the gapping appearance characteristic of *Echinacea paradoxa*. The habit of these newly created plants was unexpectedly more compact and well-branched, typical of G0052Y plants, their backcross parent. The $F_2BC_1F_1$ plants were organized according to their ray floret color range and relabelled with the designations E30-1 through E30-7 for orange, E31-1 through E31-6 for coral-orange, E32-1 through E32-7, E37-1 through E37-6, and E33-1 through E33-7 for red-orange, E34-1 through E34-8 for coral purple, E35-1 through E35-8 for coral, E36-1 through E36-6 for red, E38-1 through E38-11 for bright orange, E39-1 through E39-7 for yellow, and E40-1 through E40-15 for creamy yellow.

Mass crossing and recurrent selection within each color group leads to the development of *Echinacea* varieties having brightly colored ray florets including, but not limited to colors of orange, coral-orange, red-orange, red, and yellow.

Example 5

Crosses of G0052Y Parental Lines and *Echinacea hybrida* Plants

In 2004, plants designated E05-11-6, E05-2-4, E05-1-1, were crossed with the commercial varieties *Echinacea hybrida* 'Art's Pride', U.S. Plant Pat. No. 15,090, *Echinacea hybrida* 'Sunset', U.S. Plant Pat. No. 16,424, and *Echinacea hybrida* 'Sunrise', U.S. Plant Pat. No. 16,235. All of the vegetative varieties have pedigrees that include the species *Echinacea purpurea* and *Echinacea paradoxa*. Plants designated E05-11-6, E05-2-4, E05-1-1 were in the pedigree of G0052Y. Seeds from the cross were collected and sown and the resulting $F_1$ plants were grown in the field in 2005. The progeny exhibited large, purple-pink colored ray florets. Plants were tall with an open growth habit, and poorly branched. Twenty-three $F_1$ plants were selected and designated E13-1 through E13-16, and E14-1 through E14-7. These plants were massed as previously described, seeds were harvested, sown, and $F_2$ progeny were grown in field conditions in 2006. The progeny segregated for purple, rose, and coral-red colored ray florets.

Further Embodiments of the Invention

This invention also is directed to methods for producing an *Echinacea* plant by crossing a first parent *Echinacea* plant with a second parent *Echinacea* plant wherein either the first or second parent *Echinacea* plant is G0052Y of the present invention. Further, this invention also is directed to methods for producing a hybrid *Echinacea*-derived plant by crossing G0052Y with a second *Echinacea* plant and growing the progeny seed, and repeating the crossing and growing steps with either the first or second parent plant from 1, 2, 3, 4, 5, 6 to 7 times. Thus, any such methods using G0052Y are part of this invention: selfing, backcrosses, hybrid production, crosses to populations, and the like. All plants produced using a G0052Y as a parent are within the scope of this invention, including plants derived from hybrids of G0052Y.

As used herein, the term plant includes plant cells, plant protoplasts, plant cell tissue cultures from which *Echinacea* plants can be regenerated, plant calli, plant clumps and plant cells that are intact in plants or parts of plants, such as embryos, pollen, ovules, flowers, pistils, anthers, leaves, stems, and the like.

Additional Breeding Methods for *Echinacea*

One method of recurrent selection entails individual plants cross pollinating with each other to form progeny. The progeny are grown and the superior progeny selected by any number of selection methods, which include individual plant, half-sib progeny, full-sib progeny, selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids.

Mass selection can be used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Backcross breeding can be used to move the progeny toward the genotype of the recurrent parent but at the same time retain many components of the non-recurrent parent by stopping the backcrossing at an early stage and proceeding with selfing and selection. For example, an $F_1$, such as a commercial hybrid, is created. This commercial hybrid may be backcrossed to one of its parent lines to create a $BC_1$ or $BC_2$. Progeny are selfed and selected so that the newly developed inbred has many of the attributes of the recurrent parent and yet several of the desired attributes of the non-recurrent parent.

Pedigree breeding starts with the crossing of two genotypes, such as a plant from G0052Y and one other elite line having one or more desirable characteristics that is lacking or which complements G0052Y. If the two original parents do not provide all the desired characteristics, other sources can be included in the breeding population. In the pedigree method, superior plants are selfed and selected in successive filial generations.

Pedigree is a method used by breeders of ordinary skill in the art to describe the varieties. Varieties that are more closely related by pedigree are likely to share common genotypes and combinations of phenotypic characteristics. All breeders of ordinary skill in the art maintain pedigree records of their breeding programs. These pedigree records contain a detailed description of the breeding process, including a listing of all parental lines used in the breeding process and information on how such line was used. A breeder of ordinary skill in the art would know if G0052Y was used in the development of a progeny line, and would also know how many crosses to a line other than G0052Y or to G0052Y as a parent or other progenitor were made in the development of any progeny line.

Mutation breeding is one of many methods that could be used to introduce new traits into plants derived from G0052Y. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of the G0052Y that comprises such mutation.

Traits are also used by those of ordinary skill in the art to characterize progeny. Traits are commonly evaluated at a significance level, such as a 1%, 5% or 10% significance level, when measured in plants grown in the same environmental conditions. For example, a mutant or backcross conversion of G0052Y may be characterized as having the same morphological and physiological traits as G0052Y. The traits used for comparison may be any or all of the traits shown in Table 1.

Breeding With Molecular Markers

Molecular markers also provide a means by which those of ordinary skill in the art characterize the similarity or differences of two lines. Using the breeding methods described herein, one can develop individual plants, plant cells, and populations of plants that retain at least 25% and, up to 99.5% genetic contribution from G0052Y, as measured by either percent identity or percent similarity. In pedigree analysis the percentage genetic contribution may not be actually known, but on average 50% of the starting germplasm would be expected to be passed to the progeny line after one cross to another line, 25% after another cross to a different line, and so on. With backcrossing, the expected contribution of G0052Y after 2, 3, 4 and 5 doses (or 1, 2, 3 and 4 backcrosses) would be 75%, 87.5%, 93.75% and 96.875% respectively. Actual genetic contribution may be much higher than the genetic contribution expected by pedigree, especially if molecular markers are used in selection. Molecular markers could also be used to confirm and/or determine the pedigree of the progeny line.

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing G0052Y.

Isozyme Electrophoresis and RFLPs have been widely used to determine genetic composition. Isozyme Electrophoresis has a relatively low number of available as markers and a low number of allelic variants. RFLPs allow more discrimination because they have a higher degree of allelic variation. Both of these methods have been eclipsed by SSRs SSR technology is more efficient and practical to use than RFLPs; more marker loci can be routinely used and more alleles per marker locus can be found using SSRs in comparison to RFLPs. Single Nucleotide Polymorphisms may also be used to identify the unique genetic composition of the invention and progeny lines retaining that unique genetic composition. Various molecular marker techniques may be used in combination to enhance overall resolution.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection.

All plants produced by the use of the methods described herein and that retain the unique genetic or trait combinations of G0052Y are within the scope of the invention. Progeny of the breeding methods described herein may be characterized in any number of ways, such as by traits retained in the progeny, pedigree and/or molecular markers. Combinations of these methods of characterization may be used.

Tissue Culture

As it is well known in the art, tissue culture of *Echinacea* can be used for the in vitro regeneration of *Echinacea* plants. Tissues cultures of various tissues of *Echinacea* and regeneration of plants therefrom are well known and published. By way of example, a tissue culture comprising organs has been used to produce regenerated plants as described in In Vitro Regeneration and *Agrobacterium* Transformation of *Echinacea purpurea* Leaf Explants, Korock, A. et al., 2002, in J. Janick and A. Whipkey (eds.), *Trends in new crops and new uses*, p 522-526; Regeneration and Micropropagation: Techniques, Systems and Media 1991-1995, in Herman, E. B., ed., *Recent Advances in Plant Tissue Culture*, Volume 3 (1995); Desamero et al., *Plant Cell Tiss. Org. Cult.* 33:265-271 (1993); Tabei et al., *Plant Tiss. Cult. Lett.* 10:235 (1993). Thus, another aspect of this invention is to provide cells which, upon growth and differentiation, produce *Echinacea* plants having the physiological and morphological characteristics of *Echinacea purpurea* G0052Y.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, petioles, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

With the advent of molecular biological techniques allowing the isolation and characterization of genes that encode specific protein products, scientists in the field of plant biology developed a strong interest in engineering the genome of plants to contain and express foreign genes, or additional or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention in particular embodiments also relates to transformed versions of the claimed plants of *Echinacea purpurea* G0052Y and progeny therefrom.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed *Echinacea* plants, using transformation methods as described below to incorporate transgenes into the genetic material of the *Echinacea* plant(s).

Expression Vectors for *Echinacea* Transformation—Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which, when placed under the control of plant regulatory signals, confers resistance to kanamycin. Fraley et al., *Proc. Natl. Acad. Sci. U.S.A.*, 80:4803 (1983) Eck et al., *Plant Cell Report*, 14:5 299-304 (1995). Another commonly used selectable marker gene is the hygromycin phosphotransferase gene which confers resistance to the antibiotic hygromycin. Vanden Elzen et al., *Plant Mol Biol.*, 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Selectable marker genes for plant transformation which are not of bacterial origin include, for example, mouse dihydrofolate reductase, plant 5-enol-pyruvyl-shikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), alpha-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984), Charng et al., *Plant Science Limerick.* 1994, 98: 2, 175-183, Hu Wei e al., *In vitro Cellular and Developmental Biology Plant* 37:112-18 (2001), Agharbaoui et al., *Plant Cell Report* 15:1/2 102-105 (1995).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for *Echinacea* Transformation—Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A plant promoter is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in *Echinacea*. Optionally, the inducible promoter is operably linked to a nucleotide sequence encoding a signal sequence which is operably linked to a gene for expression in *Echinacea*. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227: 229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters

A constitutive promoter is operably linked to a gene for expression in *Echinacea* or the constitutive promoter is operably linked to a nucleotide sequence encoding a signal sequence which is operably linked to a gene for expression in *Echinacea*.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985), Tababeizadeh et al., *Plant Cell Report* 19:2 197-202 (1999), Kunik et al., *Acta Horticulturae* 447, 387-391 (1997)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, XbaI/NcoI fragment, 5' to the *Brassica napus* ALS3 structural gene (or a nucleotide sequence similar to said XbaI/NcoI fragment), represents a particularly useful constitutive promoter. See PCT application WO 96/30530.

C. Tissue-specific or Tissue-preferred Promoters

A tissue-specific promoter is operably linked to a gene for expression in *Echinacea*. Optionally, the tissue-specific promoter is operably linked to a nucleotide sequence encoding a signal sequence which is operably linked to a gene for expression in *Echinacea*. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)), such as the promoter rolD from *Agrobacterium rhizogenes* as mentioned in Grichko et al., *Plant Physiology and Biochemistry* 39:1 19-25 (2001); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zml3 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3-17 (1987); Lemer et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Methods for *Echinacea* Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation

One method for introducing an expression vector into plants is based on the natural transformation system of *Agrobacterium*. See, for example, In Vitro Regeneration and *Agrobacteriur* Transformation of *Echinacea purpurea* Leaf Explants, Korock, A. et al., 2002, in J. Janick and A. Whipkey (eds.), *Trends in new crops and new uses*, p 522-526; Frary et al., *Plant Cell Report*. 1996, 16: 3/4, 235-240, Roehel et al., *Plant Cell Report*. 1993, 12: 11, 644-647, Hu-Wei et al., *In Vitro Cellular and Developmental Biology Plant*. 2001 37: 1, 12-18. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 6,198,022 issued Mar. 6, 2001.

B. Direct Gene Transfer

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992), Baum et al., *Plant Journal.* 1997, 12: 2, 463-469, Eck et al., *Plant Cell Report.* 1995, 14: 5, 299-304, Manzara et al., *Plant Molecular Biology Reporter* 123: 221-226 (1994).

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues has also been described. Donn et al., In Abstracts of VIIth International Congress on Plant Cell and Tissue Culture IAPTC, A2-38, p 53 (1990), D'Halluin et al., *Plant Cell* 4:1495-1505 (1992) and Spencer et al., *Plant Mol. Biol.* 24:51-61 (1994). A transfer of chromosomes has been reported from a transformed donor line of potato to a recipient line of tomato through microprotoplast PEG induced fusion. See Ramalu et al., *Theoretical and Applied Genetics* 92:316-325 (1996).

Following transformation of *Echinacea* target tissues, expression of the above-described selectable marker genes allows for preferential selection of transformed cells, tissues and/or plants, using regeneration and selection methods now well known in the art.

The foregoing methods for transformation would typically be used for producing a transgenic plant. The transgenic plant could then be crossed with another (non-transformed or transformed) plant in order to produce a new transgenic plant. Alternatively, a genetic trait which has been engineered into a particular *Echinacea* variety or hybrid using the foregoing transformation techniques could be moved into another *Echinacea* variety or hybrid using traditional backcrossing techniques that are well known in the plant breeding arts. For example, a backcrossing approach could be used to move an engineered trait from an *Echinacea* variety or hybrid containing a foreign gene in its genome into an *Echinacea* variety or hybrid which does not contain that gene. As used herein, "crossing" can refer to a simple X by Y cross, or the process of backcrossing, depending on the context.

Persons of ordinary skill in the art will recognize that when the term *Echinacea* plant is used in the context of the present invention, this also includes derivative varieties that retain the essential distinguishing characteristics of *Echinacea purpurea* G0052Y, such as a Single Gene Converted (Conversion) plant of G0052Y or a transgenic derivative having one or more value-added genes incorporated therein (such as herbicide or pest resistance). Backcrossing methods can be used with the present invention to improve or introduce a characteristic into the variety. The term "backcrossing" as used herein refers to the repeated crossing 1, 2, 3, 4, 5, 6, 7, 8, 9 or more times of a hybrid progeny back to the recurrent parents. The parental *Echinacea* plant which contributes the gene for the desired characteristic is termed the nonrecurrent or donor parent. This terminology refers to the fact that the nonrecurrent parent is used one time in the backcross protocol and therefore does not recur. The parental *Echinacea* plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until an *Echinacea* plant is obtained wherein essentially all of the desired morphological and physiological characteristics of the recurrent parent are recovered in the converted plant, in addition to the single gene transferred from the nonrecurrent parent, as determined at the 5% significance level when grown under the same environmental conditions.

Changing Phenotypes in Plants by Changing Expressions of Genes

Changes in plant phenotypes can be produced by inhibiting expression of one or more genes or by overexpressing one or more genes. Various promoters, targeting sequences, enhancing sequences, and other DNA sequences can be inserted into the *Echinacea* genome for the purpose of altering the expression of genes which results in altered flower color and/or altered flower color pattern similar to the flower color and/or flower color pattern produced by the *Echinacea* plant of the present invention.

Specifically inhibiting expression of one or more genes (also known as gene silencing, or gene suppression) can be accomplished by antisense inhibition or cosuppression (U.S. Pat. Nos. 5,190,931, 5,107,065 and 5,283,323). An antisense gene is a complete (full length) coding sequence of the gene of interest or a fragment thereof. An antisense gene may also be to an untranslated portion of an endogenous plant gene, such as a 5' untranslated leader region or a 3' untranslated terminator or polyadenylation region of the gene as it exists in plants. Expression of a transgenic antisense sequence allows for the regulation of the specific endogenous plant gene of interest. Antisense inhibition was first reported in electroporation of carrot protoplasts with antisense and sense constructs containing the CAT reporter gene resulted in varying inhibition of CAT activity dependent on promoter strength (Ecker et al., *Proc. Natl. Acad. Sci. U.S.A.* 83: 5372 5376, 1986). A stable inheritable antisense effect was first reported in tobacco using the NOS transgene (Rothstein et al., *Proc. Natl. Acad. Sci. U.S.A.* 84: 8439 8943, 1987). Constitutive expression of antisense chalcone synthase (CHS) in transgenic tobacco and petunia plants decreased endogenous CHS RNA and protein activity demonstrating the application of this technology in regulating endogenous gene expression (van der Krol et al., *Nature* 333: 866 869, 1988; van der Krol et al., *Plant Molecular Biology* 14: 457 466, 1990).

Many techniques for gene silencing are well known to one of skill in the art, including but not limited to knock-outs (such as by insertion of a transposable element such as mu (V. Chandler, The Maize Handbook, Springer-Verlag 1994) or other genetic elements such as a FRT, Lox or other site specific integration site, antisense technology (see, e.g., Sheehy et al. (1988) PNAS USA 85:8805 8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340 344; Flavell (1994) *PNAS USA* 91:3490 3496; Finnegan et al. (1994) *Bio/Technology* 12: 883 888; and Neuhuber et al. (1994) *Mol. Gen. Genet.* 244:230 241); RNA interference (Napoli et al. (1990) Plant Cell 2:279 289; U.S. Pat. No. 5,034,323; Sharp (1999) *Genes Dev.* 13:139 141; Zamore et al. (2000) Cell 101:25 33; and Montgomery et al. (1998) PNAS USA 95:15502 15507), virus-induced gene silencing (Burton, et al. (2000) Plant Cell 12:691 705; and Baulcombe (1999) Curr. Op. Plant Bio. 2:109 113); target-RNA-specific ribozymes (Haseloff et al. (1988) Nature 334: 585 591); hairpin structures (Smith et al. (2000) Nature 407: 319 320; WO 99/53050; and WO 98/53083); MicroRNA (Aukerman & Sakai (2003) Plant Cell 15:2730 2741); ribozymes (Steinecke et al. (1992) EMBO J. 11:1525; and Perriman et al. (1993) Antisense Res. Dev. 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Overexpression of various genes in Echinacea which result in altered flower color and/or altered flower color pattern may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression. See for example, Jefferson, R. A., 1987. Assaying chimeric genes in plants: the GUS gene fusion system. Plant Mol. Biol. Rpt. (5):387-405.

Cosuppression, also known as cosense suppression, homology-dependent gene silencing, repeat-induced gene silencing, et cetera, is the inactivation of a gene in a cell where it is normally functional and may be used for altering flower color and/or altering flower color pattern for example, in petunia (for reviews see Baulcombe et al., Current Opinion Biotechnol. 7: 173 180, 1996; Meyer et al., Annu. Rev. Plant Physiol. Plant Mol. Biol. 47: 23 48, 1996; Matzke et al., Plant Physiol. 107: 679 685, 1995). Transgene induced cosuppression in plants has been shown to have useful effects which include reduced impact of viral infection, fruit ripening, affecting flower color, inactivation of infecting transposons and retrotransposons, and editing aberrant RNA transcripts (Smyth et al., Current Biol. 7: 793 795, 1997; Napoli et al., Plant Cell 2: 279 289, 1990). Many examples of cosuppression have been reported in the literature: sense suppression of caffeic acid O-methyltransferase resulted in altered stem coloration of aspen (Tsai et al., Plant Physiology 117: 101112, 1998); cosuppression of a lipoxygenase isozyme (LOX2) resulted in transgenic Arabidopsis plants unable to accumulate jasmonic acid following wounding (Bell et al., Proc. Natl. Acad. Sci. U.S.A. 92: 8675 8679, 1995); cosuppression of phytochrome-regulated chlorophyll .alpha./.beta. 140 RNA levels in Arabidopsis (Brussian et al., Plant Cell 5: 667 677, 1993); cosuppression of a pea cDNA encoding light-activated chloroplast NADP-malate dehydrogenase in transgenic tobacco (Faske et al., Plant Physiol. 115: 705 715, 1997); cosuppression of Flaveria bidentis NADP-MDH via heterologous sorghum NADP-MDH cDNA despite only about 71% sequence homology (Trevanion et al., Plant Physiol. 113: 1153 1163, 1997); cosuppression of a proline-rich glycoprotein (TTS) involved in pollen tube growth in transgenic tobacco (Cheung et al., Cell 82: 383 393, 1995); cosuppression of phenylalanine ammonia-lyase (PAL) in transgenic tobacco (Elkind et al., Proc. Natl. Acad. Sci. U.S.A. 87: 9057 9061); and cosuppression of two MADS box floral binding protein genes (FBP7 and FBP11) in petunia (Colombo et al., Plant Cell 9: 703 715, 1997).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is Echinacea. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, plant genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science 266:789 (1994) (cloning of the tomato Cf-9 gene for resistance to Cladosporium fulvum); Martin et al., Science 262:1432 (1993) (tomato Pto gene for resistance to Pseudomonas syringae pv. tomato encodes a protein kinase); Mindrinos et al., Cell 78:1089 (1994) (Arabidopsis RSP2 gene for resistance to Pseudomonas syringae).

B. A gene conferring resistance to a pest, such as soybean cyst nematode. See e.g., PCT Application WO 96/30517; PCT Application WO 93/19181.

C. A Bacillus thuringiensis protein, a derivative thereof or a synthetic polypeptide modeled thereon. See, for example, Geiser et al., Gene 48:109 (1986), who disclose the cloning and nucleotide sequence of a Bt alpha-endotoxin gene. Moreover, DNA molecules encoding alpha-endotoxin genes can be purchased from American Type Culture Collection, Manassas, Va., for example, under ATCC Accession Nos. 40098, 67136, 31995 and 31998.

D. A lectin. See, for example, the article by Van Damme et al., Plant Molec. Biol. 24:25 (1994), who disclose the nucleotide sequences of several Clivia miniata mannose-binding lectin genes.

E. A vitamin-binding protein such as avidin. See PCT application US93/06487. The application teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* alpha-amylase inhibitor).

G. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyper-accumulation of a monoterpene, a sesquiterpene, a steroid, a hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., *Plant Sci* 89:43 (1993), of heterologous expression of a cecropin-beta, lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect.

A. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo-alpha-1,4-D-polygalacturonases facilitate fungal colonization and plant nutrient release by solubilizing plant cell wall homo-alpha-1,4-D-galacturonase. See Lamb et al., *BioTechnology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *BioTechnology* 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S. *Current Biology,* 5(2) (1995).

U. Antifungal genes. See Cornelissen and Melchers, Plant Physiol., 101:709-712 (1993); Parijs et al., *Planta* 183:258-264 (1991) and Bushnell et al., *Can. J. of Plant Path.* 20(2): 137-149 (1998).

2. Genes That Confer Resistance to an Herbicide, For Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvylshikimate-3-phosphate synthase (EPSP) and aroA genes, respectively) and other phosphono compounds such as glufosinate(phosphinothricin acetyl transferase (PAT) and *Streptomyces hygroscopicus* PAT bar genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *BioTechnology* 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Accl-S1, Accl-S2 and Accl-S3 genes described by Marshall et al., *Theor. Appl. Genet.* 83:435 (1992).

C. An herbicide that inhibits photosynthesis, such as a triazine (psbA and gs+ genes) or a benzonitrile(nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase(protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes That Confer or Contribute to a Value-Added Trait, Such as:

A. Increased resistance/tolerance to water stress or drought, for example, by transforming a plant to create a plant having a modified content in ABA-Water-Stress-Ripening-Induced proteins (ARS proteins) as described in WO 01/83753 in the name of Biogemma, or by transforming a plant with a nucleotide sequence coding for a phosphoenolpyruvate carboxylase as shown in WO 02/081714. The tolerance of corn to drought can also be increased by an overexpression of phosphoenolpyruvate carboxylase (PEPC-C4), obtained, for example from sorghum.

B. Increased content of cysteine and glutathione, useful in the regulation of sulfur compounds and plant resistance against various stresses such as drought, heat or cold, by transforming a plant with a gene coding for an Adenosine 5' Phosphosulfate as shown in WO 01/49855.

4. Genes that Control Male Sterility

A. Introduction of a deacetylase gene under the control of a tapetum-specific promoter and with the application of the chemical N—Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

DEPOSIT INFORMATION

A deposit of the Ball Horticultural Company proprietary *Echinacea purpurea* G0052Y disclosed above and recited in the appended claims has been made with the American Type Culture Collection (ATCC), 10801 University Boulevard, Manassas, Va. 20110. The date of deposit was Aug. 12, 2008.

The deposit of 2,500 seeds was taken from the same deposit maintained by Ball Horticultural Company since prior to the filing date of this application. All restrictions will be removed upon granting of a patent, and the deposit is intended to meet all of the requirements of 37 C.F.R. §§1.801-1.809. The ATCC Accession Number is PTA-9415. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of an *Echinacea purpurea* designated G0052Y, wherein a representative sample of said seed was deposited under ATCC Accession No. PTA-9415.

2. An *Echinacea purpurea* plant, or a part thereof, produced by growing the seed of claim 1.

3. A tissue culture of cells produced from the plant of claim 2, wherein said cells of the tissue culture are produced from a plant part selected from the group consisting of leaf, pollen, embryo, cotyledon, hypocotyl, meristematic cell, root, root tip, anther, pistil, flower, and stem.

4. An *Echinacea* plant regenerated from the tissue culture of claim 3, wherein the plant has all the morphological and physiological characteristics of *Echinacea purpurea* G0052Y.

5. An *Echinacea* plant, or a part thereof, having all of the physiological and morphological characteristics of G0052Y.

6. A method of producing *Echinacea* seed, comprising crossing a first parent *Echinacea* plant with a second parent *Echinacea* plant, wherein one or both of the first or the second parent *Echinacea* plants is the plant of claim 2 and, wherein seed is allowed to form.

7. An *Echinacea* seed produced by the method of claim 6.

8. The *Echinacea* seed of claim 7, wherein the *Echinacea* seed is hybrid seed.

9. A hybrid *Echinacea* plant, or a part thereof, produced by growing said hybrid seed of claim 8.

10. An *Echinacea* plant produced by introducing at least one single gene conversion into the plant of claim 2 by transformation or backcrossing.

11. The *Echinacea* plant of claim 10, wherein the gene is selected from the group consisting of a dominant allele and a recessive allele.

12. The *Echinacea* plant of claim 10, wherein the gene confers a trait selected from the group consisting of herbicide tolerance, insect resistance, resistance to bacterial, fungal, nematode or viral disease, male sterility and restoration of male fertility.

13. A method of producing an *Echinacea* plant comprising the steps of:
    (a) crossing the plant of claim 2 with a second *Echinacea* plant to produce a progeny seed;
    (b) growing said progeny seed to produce a progeny plant;
    (c) crossing the progeny plant with itself or a different *Echinacea* plant to produce further progeny seed of a subsequent generation; and
    (d) growing said further progeny seed to produce a further progeny plant.

14. The method of claim 13, further comprising crossing the said progeny plants with a second, distinct *Echinacea* plant to produce an $F_1$ hybrid *Echinacea* plant.

15. A method for developing a second *Echinacea* plant in an *Echinacea* plant breeding program comprising applying plant breeding techniques to a first *Echinacea* plant, or a part thereof, wherein said first *Echinacea* plant is the *Echinacea* plant of claim 5, and wherein application of said techniques results in development of said second *Echinacea* plant.

16. The method for developing a *Echinacea* plant in an *Echinacea* plant breeding program of claim 15 wherein plant breeding techniques are selected from the group consisting of mass selection, recurrent selection, backcrossing, pedigree breeding, restriction fragment length polymorphism enhanced selection, genetic marker enhanced selection, and transformation.

17. A method of producing an *Echinacea* plant comprising the steps of:

(a) crossing the plant of claim 2 with a second *Echinacea* plant to produce progeny seed;

(b) growing said progeny seed to produce one or more sib progeny plants;

(c) conducting mass-pollination among the said sib progeny plants to produce further progeny *Echinacea* seed of a subsequent generation; and (d) growing said further progeny seed to produce a further progeny plant.

* * * * *